United States Patent [19]
Laird et al.

[11] 3,991,627
[45] Nov. 16, 1976

[54] ALIGNMENT DEVICE FOR SAMPLE CONTAINERS

[75] Inventors: Cleve Watrous Laird, Acton; Noboru Matsu, Marblehead, both of Mass.

[73] Assignee: Block Engineering, Inc., Cambridge, Mass.

[22] Filed: Nov. 28, 1975

[21] Appl. No.: 636,157

[52] U.S. Cl. ............................... 73/423 R; 23/259; 73/432 R; 73/425.6
[51] Int. Cl.² ......................................... G01N 1/10
[58] Field of Search ............... 73/423 R, 425.6, 432; 141/165, 312, 369, 372; 23/259, 292; 128/2 F, 276; 206/305; 233/26; 211/74

[56] References Cited
UNITED STATES PATENTS

| | | |
|---|---|---|
| 3,518,164 | 6/1970 | Andelin et al. ........................ 23/292 |
| 3,527,101 | 9/1970 | Sprunger et al. ................ 73/423 A |
| 3,918,920 | 11/1975 | Barber .................................. 23/292 |

*Primary Examiner*—S. Clement Swisher
*Attorney, Agent, or Firm*—Schiller & Pandiscio

[57] ABSTRACT

A device for aligning sample containers (particularly of the test tube type) regardless of the container's size, comprises a foot member provided with a tapered cavity for receiving the bottom end of the container, a holder for holding the other end of the container in a temporary position, and a head member having a tapered cavity for receiving the other or upper end of the container. The foot and head members are movable relative to one another so that the cavity of the head member can releasably engage the upper end of the container and align the container with a predetermined axis. The device can be used to mix and test sample fluids, as well as dispense and aspirate fluids into and out of the containers.

35 Claims, 16 Drawing Figures

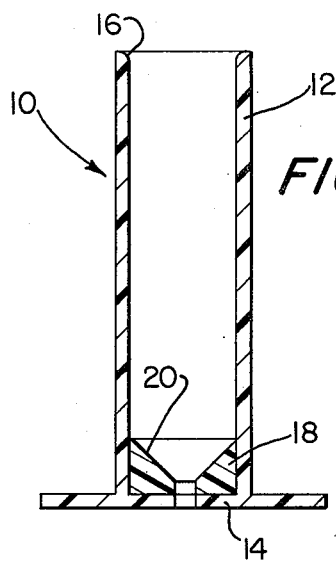
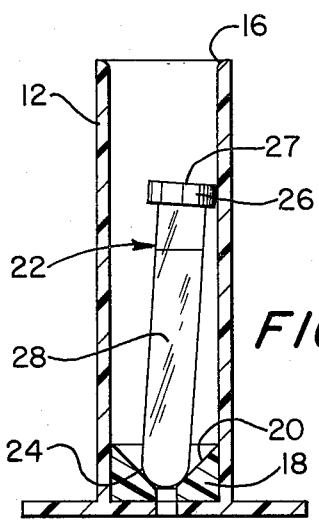
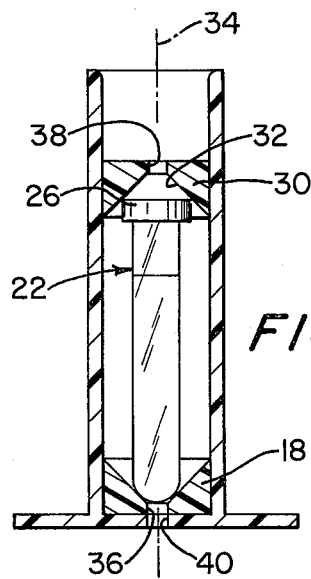
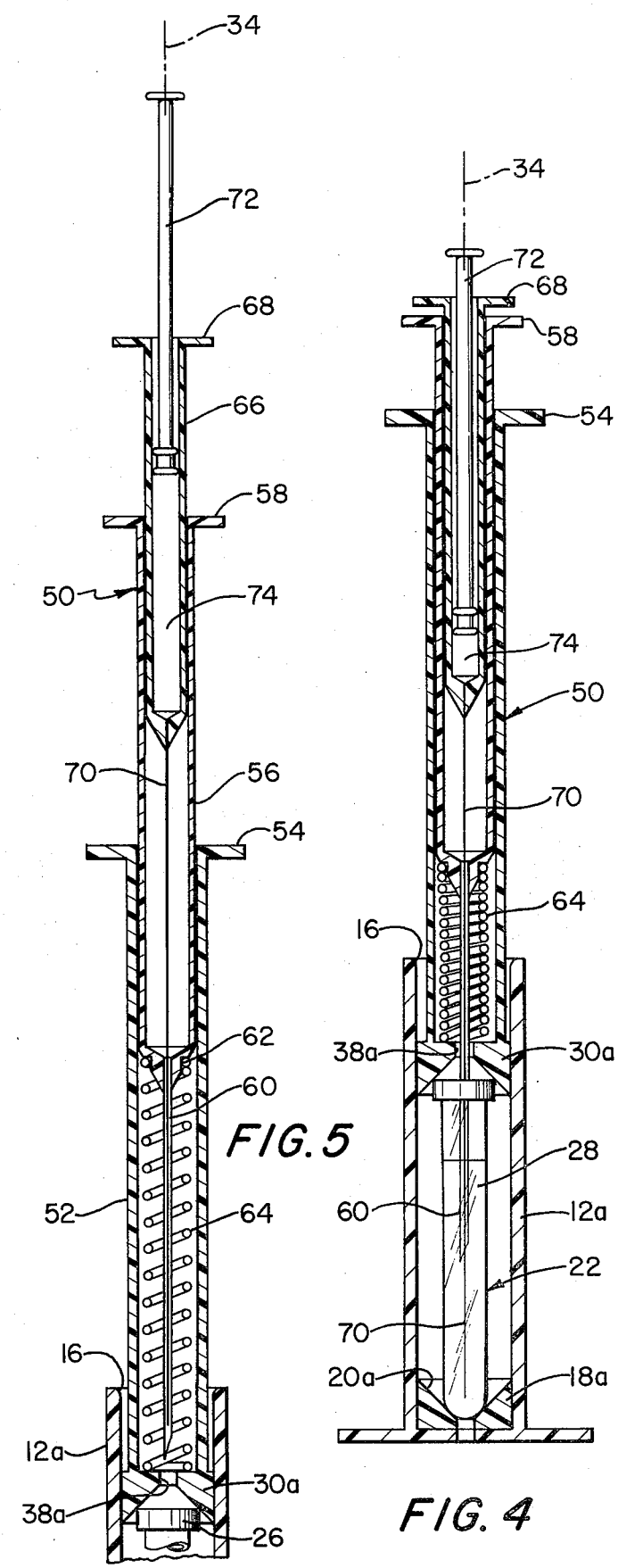

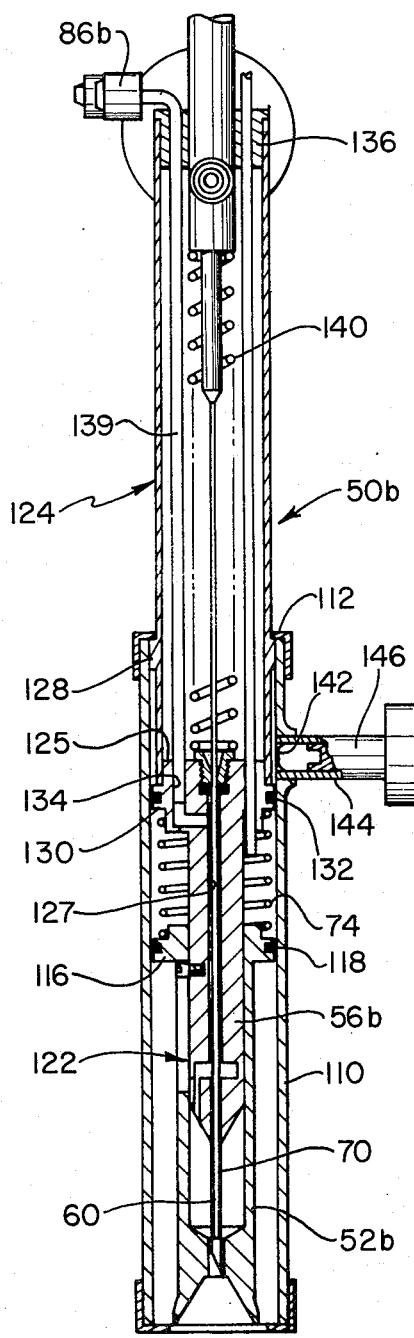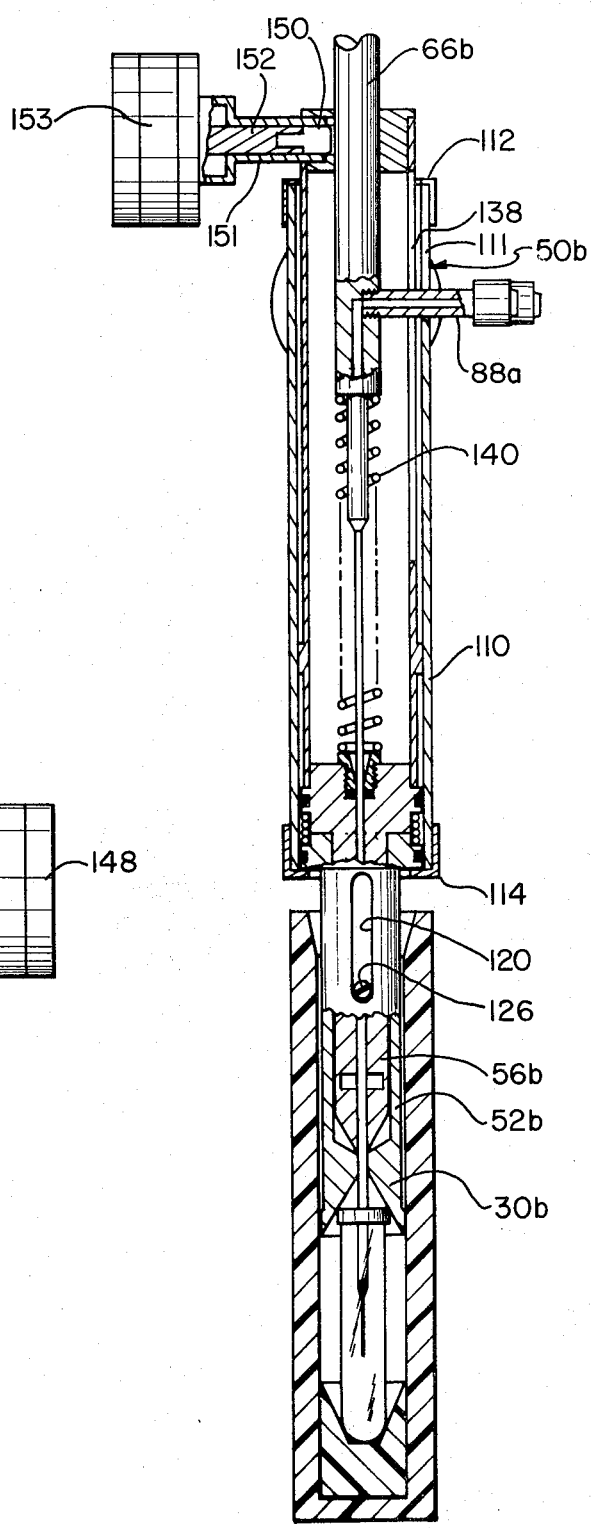
FIG. 8
FIG. 9

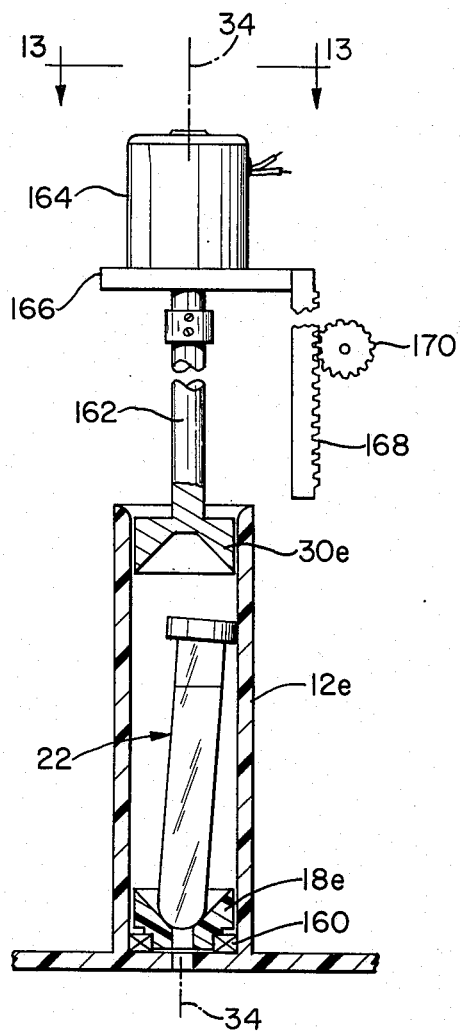
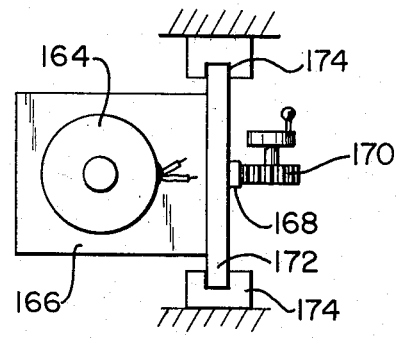
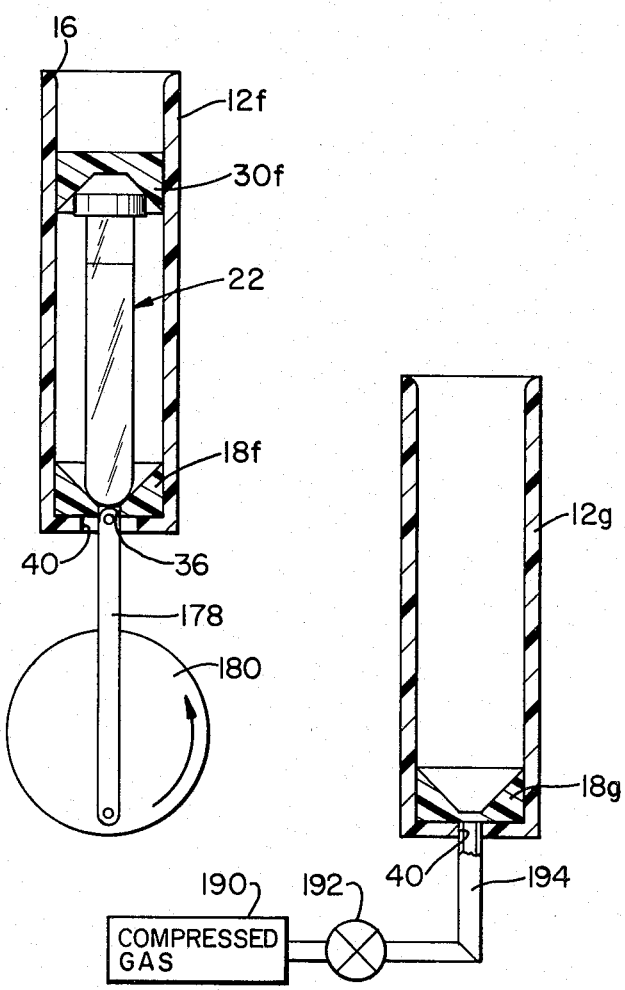

ALIGNMENT DEVICE FOR SAMPLE CONTAINERS

This invention relates to sampling and testing systems and more particularly to devices for aligning sample containers, particularly of the test tube type, regardless of the container's size, and for dispensing, aspirating, mixing and testing sample materials provided in such containers.

Various medical and biological testing facilities have an ever increasing problem arising from the fact that various types of samples are frequently provided in various sized sample containers, usually of the test tube type. Prior to the present invention, the containers, which usually include a puncturable sealing septum over one end to insure an aseptic environment for the sample, must be placed in groups according to size and shape, especially when the containers are used with automated equipment. After being grouped, all the containers must be held in place and centered so that samples can be mixed, or so that a probe means (e.g., a cannula or a PH electrode) can be inserted through the septum into the sample in order to withdraw or add material to the container or to test the material present in the container. The various sized containers are thus difficult to handle and problems arise in properly placing, centering and retrieving the containers from known mixing, aspirating, dispensing and testing equipment.

The primary object of the present invention, therefore, is to provide a device for centering elongate sample containers, regardless of their size (within some range of sizes) so that they may be easily placed and oriented along a predetermined axis.

Another object of the present invention, is to provide an improved aspirating and dispensing device which is adapted to be used with elongate containers of various sizes and which easily and automatically locates and centers the containers so that material can be dispensed into and/or withdrawn from the containers, substantially regardless of the container's size.

Yet another object of the present invention is to provide an improved mixing device which is adapted to be used with elongated containers of various sizes and which easily and automatically locates and centers the containers so that material can be mixed.

Still another object of the present invention is to provide an improved testing apparatus which is adapted to be used with elongate containers of various sizes and which easily and automatically centers the containers so that material can be easily tested in the containers.

These and other objects are accomplished by a centering device comprising means defining a first "tapered cavity" and means defining a second "tapered cavity" for respectively receiving the opposite ends of any one of several various-sized elongate sample containers. The term "tapered cavity" as used herein is intended to describe any type of cavity, hole or the like having at least one open end at which the minimum normal cross-sectional dimension is greater than the minimal normal cross-sectional dimension adjacent the opposite end of the cavity. The dimensions of each cavity in the device of the present invention are such that the minimum normal cross-sectional dimensions at the open end of the cavity is greater than the maximum normal cross-sectional dimension of the end of any one of the containers which the particular cavity is adapted to receive, the minimum normal cross-sectional dimension adjacent the opposite end of the cavity being smaller than the maximum normal cross-sectional dimension of the end of any one of the containers to which the particular cavity is adapted to receive. The cavities may take various geometrical shapes and thus may have for example, a spherical, conical or a frustoconical configuration. The centering device also is provided with means for holding one end of the container in one of the cavities while the cavities are moved relative to one another, so that the other of the two cavities engages the other end of the container and moves the container into alignment with a predetermined axis.

The aspirating, dispensing, mixing and testing apparatus of the present invention utilizes the centering device to support and orient various sized containers along a predetermined axis.

Other objects of the invention will in part be obvious and will in part appear hereinafter. The invention accordingly comprises the apparatus possessing the construction, combination of elements, and arrangement of parts which are exemplified in the following detailed disclosure, and the scope of the application of which will be indicated in the claims.

For a fuller understanding of the nature and objects of the present invention, reference should be had to the following detailed description taken in connection with the accompanying drawings wherein:

FIGS. 1 – 3 illustrate cross-sectional views of the preferred embodiment of the present invention; and its sequence of operation;

FIG. 4 illustrates a cross-sectional view of an aspirating and dispensing apparatus in a retracted position, which utilizes the principles of the present invention;

FIG. 5 illustrates in cross-section a fragment of the apparatus of FIG. 4 in an extended position;

FIG. 8 illustrates in cross-section, a third embodiment of an aspirating and dispensing apparatus in an extended position which utilizes the principles of the present invention;

FIG. 9 illustrates the apparatus of FIG. 8 in a retracted position;

FIG. 12 illustrates in a side view, partially cross-sectioned, an embodiment of a mixing apparatus employing the principles of the present invention;

FIG. 13 illustrates a top view taken along lines 13 — 13 of FIG. 12;

FIG. 14 illustrates a side view, partially cross-sectioned of an embodiment of an apparatus employing the principles of the present invention which can be used for either mixing or ejecting the container;

FIG. 15 illustrates in a partially schematic, partially cross-sectional view of an embodiment of the present invention including means for ejecting the container.

In the drawing, the same numerals describe like parts.

Figure 6:
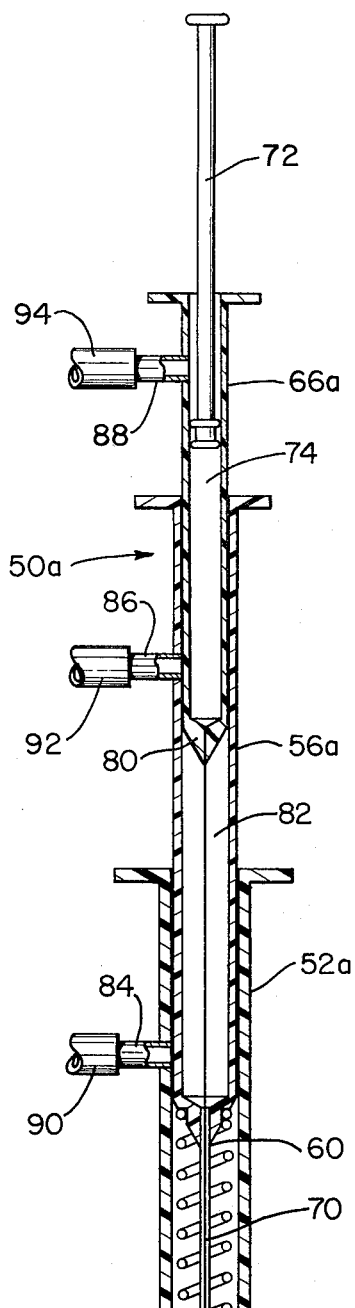
FIGS. 6 and 7 illustrate in fragmentary cross-section, a second embodiment of an aspirating and dispensing apparatus.

Referring to FIGS. 1 – 3, the principles of the present invention are described with reference to centering device 10 which includes at least one hollow, elongated tubular holder 12 at least partially closed at its bottom end by supporting base 14, and provided with a flared opening at top end 16. Holder 12 is preferably a cylinder of circular cross-section the cross-sectional diameter of which is larger than the diameter of any of the various sized containers which are to be used with the device. Although only one holder is shown, device 10 can comprise a plurality of such holders which can be arranged for example, in the form of a carrousel.

A foot member 18, preferably in the form of a cylindrical disk, is disposed at the bottom end of holder 12. Member 18 may be dimensioned to slide through holder 12 into position against base 14 or, alternatively, may be affixed in place or form part of the bottom of the holder. The foot member is provided with tapered cavity 20 facing the interior of holder 12, cavity 20 having preferably an inverted frusto-conical shape and a maximum diameter at its upper end which is approximately equal to the internal diameter of holder 12 so as to be larger than the cross-sectional diameters of any of the sample containers with which device 10 is to be used. Device 10 is particularly adapted to be used with containers of the test tube type, such as container 22 shown in FIGS. 2 and 3.

Container 22, typically has a rounded bottom end 24 and a top end 26 provided with puncturable sealing septum 27 for maintaining aseptic conditions for the fluid sample 28 contained therein. As shown in FIG. 2, when the container is dropped bottom end first through open end 16 of holder 12, rounded bottom end 24 will automatically be centered in tapered cavity 20 of foot member 18, while the top end 26 of the container will tend to lean or rest against one side of the internal wall of holder 12.

Device 10 includes head member 30, substantially identical to foot member 18, but inverted so that its tapered cavity 32 faces cavity 20. Member 30 is movable relative to foot member 22 within holder 12 along the axis 34 of elongation of the latter. As head member 30 is moved toward foot member 18, tapered cavity 32 tends to engage end 26 of the container and causes the container to reorient itself so that the upper end 26 moves from its leaning or resting position of FIG. 2 to a centered position (shown in FIG. 3) in which the general elongate direction of the container is disposed along axis 34. For reasons which will become apparent hereinafter foot and head members 18 and 30 as well as base 14 are preferably provided with apertures 36, 38 and 40 respectively, each of the latter being coaxially aligned with axis 34.

Centering device 10 thus enables one to duplicate axial positioning of any elongate sample container placed within holder 12. The cross-sectional diameter and length of the sample container makes no difference in the positioning or centering action of the device, provided that holder 12 is always longer and wider than the sample container. The centering device can be utilized for any one of a variety of purposes.

Referring to FIGS. 4 and 5, the principles of the present invention are used in connection with apparatus, designated generally at 50 for aspirating fluid 28 from container 22 or for dispensing fluids into the container. Apparatus 50 is provided with a head member 30a which is coupled to or integrally formed on the bottom end of hollow locating tube 52. Tube 52 has an outside diameter smaller than the inside diameter of holder 12a so that member 30a can be easily moved into engagement with the upper end 26 of container 22 by inserting the lower end of locating tube 52 into the upper end 16 of holder 12. The upper end of tube 52 is provided with manually engageable flanges 54. Container 22 is shown supported at its lower end within cavity 20a of foot member 18a.

A syringe body 56 having flanges 58 formed at its upper end and fitted with a trocar or piercing needle 60 at its lower end is telescopically slidably fitted within tube 52 so as to be movable between an extended position (as shown in FIG. 5) and a retracted position (as shown in FIG. 4). Trocar 60 is generally an elongate tubular needle having a tapered end and an axis of elongation substantially coincident with centering axis 34 when head member 30a is inserted into holder 12 and engages the upper end 26 of container 22. Thus, if body 56 is moved from the extended position to the retracted position, trocar 60 will move from a position above aperture 38a of headmember 30a, through aperture 38a into contact with the sealing septum 27 at the top end of container 22, piercing the septum so that the tapered end of trocar lies completely within container 22. It is noted that septum 27 of the container tends to maintain a seal around piercing trocar 60 so as to insure aseptic conditions in the interior of container 22.

In order to bias body 56 in the extended position, the bottom end of the body is preferably provided with an annular collar 62 so as to receive one end of a helical spring 64. The other end of the spring is held in place by the upper side of head member 30a. Thus, motion of body 56 from the extended position to the retracted position, places spring 64 under compression as shown in FIG. 4.

A syringe cartridge 66 is telescopically slidably mounted in body 56 between an extended position (as shown in FIG. 5) and a retracted position (as shown in FIG. 4). Cartridge 66 includes means for holding the cartridge in the form of flanges 68 which are formed at the upper end of the cartridge and also includes probe means shown typically in the form of a cannula 70 at its lower end. Cannula 70 has an axis of elongation which is substantially coincident with centering axis 34 when apparatus 50 is positioned in holder 12. The external diameter of cannula 70 is smaller than the internal diameter of trocar 60 so that cannula 70 is movable within and relative to trocar 60 along the axis 34 from the extended position, wherein cannula 70 is completely within trocar 60 and body 56 to a retracted position, wherein the bottom end of cannula 70 extends beyond the tapered end of trocar 60.

The upper end of cartridge 66 is provided with plunger 72, which together with cartridge 66 forms an aspirating and/or dispensing chamber 74. Plunger 72 is mounted coaxially with and is slidably movable with respect to cartridge 66. The lower end of plunger 72 sealingly engages the internal walls of cartridge 66 so that when the plunger is drawn from the retracted position toward the extended position, fluid may be drawn through cannula 70 into chamber 74, and when moved from the extended position toward the retracted position, fluid provided in chamber 74 can be discharged through cannula 70.

In operation, apparatus 50 can be used either for aspirating fluids from or dispensing fluids into container 22. In either event, the container 22 is placed in holder 12 in a manner as shown and described in FIG. 2. When aspirating fluids from container 22, the apparatus 50 is initially drawn to its extended position as shown in FIG. 5, with the exception that plunger 72 is pushed to its retracted position (shown in FIG. 4). Locating tube 52 is inserted into holder 12a so that head member 30a locates and centers container 22 coaxially with axis 34. Syringe body 56 is moved relative to tube 52 along axis 34 against spring 64 from the extended position to the retracted position so that the tapered end of trocar 60 moves from within tube 52, through aperture 38a into contact with septum 27 of container 22. The trocar pierces the septum and extends into the interior of the container 22. The axial movement of body 56 relative to tube 52 can be manually accomplished by holding the flanges 54 of tube 52 while pushing the flanges 58 of body 56, so that the body moves along axis 34 until trocar 60 extends into the container. Once the trocar 60 is positioned in container 22, the entire syringe cartridge 66 is moved relative to body 56 from the extended position to the retracted position so that the lower end of cannula 70 moves from within trocar 60 into container 22 within the fluid 28. Apparatus 50 is now in position to aspirate fluid 28 from the container. Plunger 72 is thus pulled relative to cartridge 66 along axis 34 from the retracted position to an extended position so as to draw fluid from container 22 through cannula 70 into chamber 74.

In order to withdraw apparatus 50, cartridge 66 is then moved along axis 34 relative to syringe body 56 from the retracted position to an extended position so that cannula 70 is drawn back into body 56 and trocar 60, and the extreme end of cannula 70 is within trocar 60. Next, syringe body 56 is moved along axis 34 from the retracted position to an extended position so that the tapered end of trocar 60 is moved from within container 22 through septum 27 of the container wherein the septum will reseal maintaining the aseptic conditions within container 22. The trocar is then drawn through aperture 38a, into locating tube 52. The movement of the syringe body 56 relative to the locating tube 52 from the retracted position to an extended position is facilitated by the action of the spring 64 which urges the body 56 to the extended position.

The operation of the apparatus 40 as a dispensing device is similar to that described above, except that the plunger 72 is initially placed in the extended position, (as in FIG. 5) with the dispensing fluid (not shown) previously provided in chamber 74. Trocar 60 and cannula 70 are inserted into container 22 in the same manner and sequence as previously described. Plunger 72 is then moved from the extended position to a retracted position forcing the dispensing fluid from chamber 74, through cannula 70 into container 22. The apparatus can then be withdrawn in the same manner and sequence as previously described.

Various modifications can be made to the aspirating and dispensing apparatus, without departing form the present invention. For example, referring to FIGS. 6 and 7, apparatus 50a is identical to the apparatus of FIGS. 4 and 5, except that locating tube 52a, syringe body 56a and syringe cartridge 66a have been modified so that an additional aspirating and dispensing chamber, as well as means for facilitating the cleaning of the device are provided. More specifically, the lower end 80 of syringe cartridge 66a which extends into body 56a is formed so that it remains in sealing engagement with the internal wall of the body 56a. Cartridge 66a functions in a similar manner as the plunger 72 in that cartridge 66a together with the syringe body 56a forms a second aspirating and dispensing chamber 82. The chamber 82 operates in a similar manner as the chamber 74 so that when the cartridge is moved relative to body 56a from its retracted position to its extended position fluid is drawn into the chamber 82 through trocar 60; and when it is moved from the extended position to its retracted position, it forces fluid from the chamber 82 out through the trocar 60. The additional aspirating and dispensing chamber can be used in various ways. For example, where two different fluids must be added to a fluid sample in the container at a predetermined time interval, the use of the double chamber apparatus 50a is desirable. The apparatus could also be used to inject a fluid from chamber 82 into the container to mix with the fluid therein, and to aspirate the resulting mixed fluid from the container into chamber 74. Other uses will be evident to those skilled in the art.

Figure 7:
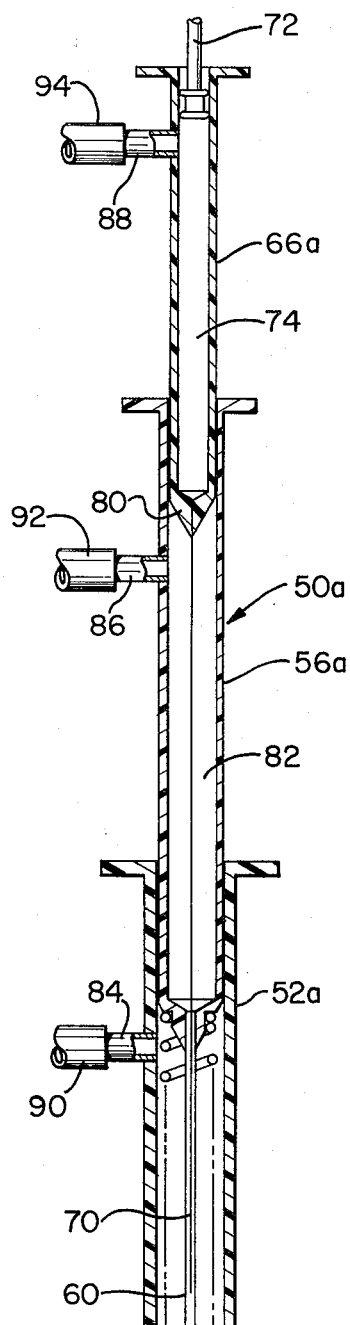

Apparatus 50a has also been modified to include means for facilitating the cleaning of the apparatus, wherein locating tube 52a, syringe body 56a, and cartridge 66a are provided with fittings 84, 86 and 88, respectively, which in turn are connected to a source of cleaning fluid (not shown) by hoses 90, 92 and 94, respectively. Fittings 84, 86, and 88 are positioned on the corresponding tube 52a, body 56a and cartridge 66a, so that when each of the tube, body and cartridge is in its normally extended operating position (as illustrated in FIG. 6), no fluid can pass through the fitting. However, by extending each of the tube, body and cartridge beyond the normally extended operating position, as shown in FIG. 7, fluid can be introduced through hoses 90, 92 and 94 in order to flush any contaminating fluids away. Specifically, by extending the apparatus to the position shown in FIG. 7, fluid introduced through hose 90 will pass through fitting 84 into locating tube 52a and wash the exterior surfaces of trocar 60, whereupon the cleaning fluid will pass out aperture 38a. Similarly, fluid introduced through hose 92 will pass through fitting 86 into chamber 82 whereupon the latter chamber and the exterior surfaces of cannula 70 are washed. The cleaning fluid also cleans the interior surfaces of trocar 60 as it passes out of chamber 82 and discharged into the locating tube 52a and out aperture 38a. Finally, cleaning fluid introduced through hose 94 and fitting 88 into chamber 74, will clean the interior surfaces of the latter chamber and when discharged from the chamber will clean the interior surfaces of cannula 70 before being discharged into locating tube 52a and out aperture 38a. After cleaning, any remaining cleaning fluid can be discharged by moving the device 50a from the position shown in FIG. 7 to the retracted position (not shown).

Various other modifications can be made to the aspirating and dispensing apparatus described with reference to FIGS. 4 – 7, without departing from the invention. Referring to FIGS. 8 and 9, apparatus 50b is provided for dispensing and aspirating fluid in and out of the container, semiautomatically. Apparatus 50b is similar to device 50a in that it includes locating tube 52b, syringe body 56b and cartridge 66b. However, various modifications have been made, wherein apparatus 50b further includes cylindrical housing 110 in which the tube, body and cartridge are coaxially mounted. Housing 110 includes a U-shaped slot 11 at its upper end for limiting the axial movement of cartridge 66b in the retracted position as will be more evident hereinafter. The housing is provided with upper and lower capped end portions 112 and 114, respectively, each of which are opened so that the tube 52b is coaxially mounted and telescopically slidable in and out of the housing. Tube 52b is provided with an annular collar 116, the latter being adapted to engage lower capped end portion 114 when device 50b is moved to its retracted position (see FIG. 8) and being provided with O-ring 118 for engaging the internal wall of the housing in a sealed manner. Tube 52b also includes an axially extending slot 120 approximately in the center of the tube the length of which defines the axial length that the body 56b moves relative to tube 52b between the extended and retracted positions.

Cartridge body 56b of device 50b has been modified to include a lower cylindrical portion 122 which is integrally joined with upper cylindrical portion 124 to form an radially inwardly directed shoulder 125. Lower cylindrical portion 122 of body 56b is telescopically slidably mounted in tube 52b and includes radially extending pin 126 which extends into slot 120 of tube 52b and limits the axial movement of the body relative to the tube. A cylindrical passageway 127 is provided axially through the center of portion 122, in which the trocar 60 is adapted to move freely. the external surface of upper cylindrical portion 124 is provided with an upper collar 128 for engaging the upper capped end portion 112 when device 50b is moved to the extended position so as to limit the axial movement of the body 56b relative to the housing 110. The external surface of portion 124 is also provided with a lower collar 130 which includes an O-ring 132 for engaging the internal wall of housing 110 in a sealing manner. Collars 116 and 130 engage and retain opposite ends of spring 74 which biases the body 56b in the extended position relative to the tube 52b. Upper cylindrical portion 124 is also provided with by-pass 134 having one end connected to passageway 127. The upper end or portion 124 includes axially-directed slot 138 (see FIG. 9) and is provided with a sealing gasket 136 which receives syringe cartridge 66b in a telescopically sliding manner.

Cartridge 66a has a smaller outside diameter than the inside diameter of the body 56b so that a fluid line 139 can extend from fitting 86b, through gasket 136, axially along the annular space provided between the body 56b and cartridge 66b to the passageway 127.

The cartridge 66b is provided with fitting 88a which extends through slot 138 of the body 56b and engages the U-shaped slot 121 of housing 110 when cartridge 66b is moved relative to body 56b to the retracted position. Helical spring 140 is provided in body 56b for biasing cartridge 66b to an extended position relative to body 56b. Specifically, spring 140 is coaxially mounted around and radially spaced from the cannula 70, with one end of the spring in contact with the radially inward shoulder 125 of tube 56b while the other end is connected to the lower end of the cartridge 66b. Spring 140 has a higher spring constant and thus is relatively stiffer than spring 74, so that spring 74 almost completely compresses before spring 140 begins compressing.

Means are also provided for locking the syringe body 56b relative to housing 110 and cartridge 66b relative to body 56b. Preferably, housing 110 is provided with an aperture 142 so that one end of hollow tube 144 can be attached thereto. The tube is oriented and its interior screw-threaded so that screw 146 having a knob 148 at one end can be turned and advanced or retracted in the tube transversely to axis 34 into and out of contact with body 56b. Similarly, the body 56b and gasket 13b are provided with apertures 150 so that one end of hollow tube 151 can be attached thereto. The tube 151 is oriented and its interior screw-threaded so that screw 152 having a knob 153 at one end can be turned and advanced or retracted in the tube transversely to axis 34 into and out of contact with cartridge 66b.

As a result of this double spring action, the device 50b of FIGS. 8 and 9 can be used for centering the container 22 and for aspirating fluids from or dispensing fluids into the container 22 in one motion. Thus, in operation, as previously described with respect to FIGS. 4 and 5 the container is placed in holder 12 in the same manner as shown and described in FIG. 2. When aspirating fluid from container 22 the apparatus 50b is initially drawn to its extended position as shown in FIG. 8. Holder 12, together with container 22 is positioned below housing 110 so that locating tube can be inserted into the holder. By moving the cartridge 66b towards the retracted position, spring 74 begins to compress and head member 30b extends into the holder so that head member 30b locates and centers container 22 coaxially with the centering axis 34. As spring 74 compresses the trocar moves through passageway 127, through aperture 38b into contact with the septum of container 22, whereupon the trocar will pierce the septum and extend into the interior of the container 22. Once the trocar 60 is positioned in container 22 and spring 74 has almost completely compressed, the pin 126 reaches the end of slot 120 and spring 140 begins to compress so that the entire syringe cartridge 66b begins to move relative to the body 56b, from the extended position to the retracted position. The extreme end of cannula 70 moves from within trocar 60 into container 22 and continues to move until fitting 88a reaches the bottom of slot 111. The cannula 70 should lie within the fluid 28 so that apparatus 50b is now in position to aspirate fluid 28 from the container. The body 56b can be held in place by rotating knob 148 so that screw 146 is advanced into engagement with the body to hold it axially with respect to housing 110, and more particularly tube 52b, the latter being urged against the top end of the container 22 by the action of spring 74. Similarly, cartridge 66b can be held in place by rotating knob 153 so that screw 152 is advanced into engagement with the cartridge to hold it axially with respect to tube 56b. The fluid may be aspirated from the container by providing a pressure on fitting 88a which is less than the pressure in container 22 so as to draw the fluid up through the cannula 70.

In order to withdraw the apparatus 50b, cartridge 66b is moved along axis 34 relative to the body 56b from the retracted position to an extended position so that the cannula 70 is drawn back into body 56b and trocar 60, and the extreme end of cannula 70 lies within trocar 60. This movement is facilitated by spring 140 which urges the cartridge 66b to an extended position relative to the body 56b. Next syringe body 56b is moved along axis 34 from the retracted position to an extended position so that the tapered end of trocar 60 is moved from within container 22 through the septum of the container wherein the septum will reseal itself. The extreme end of trocar 60 then moves through aperture 38b and back into passageway 127 of body 56b. This movement of the body 56b relative to the locating tube 52b from the retracted position to an extended position is facilitated by the action of spring 74 which urges the body 56b to the extended position relative to the locating tube 52b.

The operation of the apparatus 50b as a dispensing device is similar to that described above, except that when the trocar 60 and cannula 70 are inserted into container 22 the dispensing fluid is injected through fitting 88a into the cannula 70 where it is discharged into container 22.

Finally, the interior portion of trocar 60 and the outside of cannula 70 can be cleaned by introducing fluid through fitting 86b, along line 139, into by-pass 134, whereupon the fluid will pass through passageway 127 cleaning the outside of the cannula 70 and the inside of trocar 60. Similarly, cleaning fluid introduced through fitting 88a will clean the inside of cannula 70 before being discharged.

Figures 10, 11:
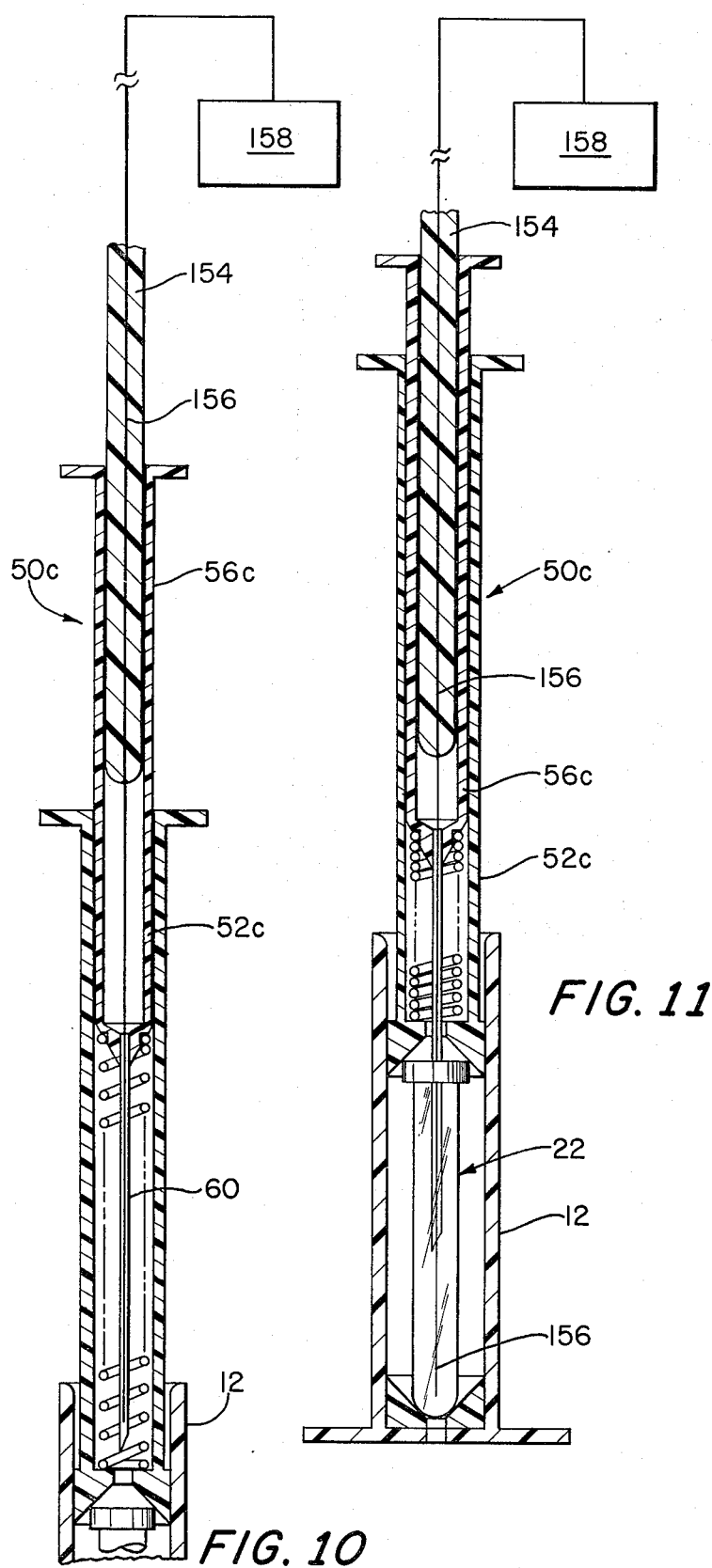
FIG. 10 illustrates in cross-section testing apparatus in an extended position employing the principles of the present invention.
FIG. 11 illustrates in cross-section the apparatus of FIG. 10 in a retracted position.

In addition to aspirating and dispensing fluid out of and into containers, the present invention can also be used for testing the sample 28. Referring to FIG. 10 and 11 a testing apparatus 50c is shown which is similar to the apparatus 50 of FIGS. 4 and 5, except that the syringe cartridge 66 and cannula 70 are replaced respectively, by plunger 154 and other probe means in the form of probe 156 and system 158. The probe and system utilized depend on the particular type of test to be performed. For example, probe 156 and system 158 may form a pH meter where the system is utilized to measure the pH of the fluid in the container 22 by immersing a pH electrode in the fluid. The probe or electrode 156 is inserted into the fluid of the container in the same manner as the cannula 70 of the FIGS. 4 and 5 embodiment. Specifically, the container is placed in the holder 12 in the same manner as previously described and shown in FIG. 2. The apparatus 50c is initially drawn to its extended position as shown in FIG. 10. Holder 12, together with a container is positioned below the apparatus so that the locating tube can be inserted into the holder. The body 56c is then moved relative to the tube 52c from the extended position to the retracted position so that the trocar 60 passes through the septum of the container. The plunger 154 is then moved from the extended position to the retracted position so that the extreme end of the probe will move out of the trocar into the fluid of the container. the system 158 can then measure the pH of the fluid. Upon completion of the test, the plunger 154 is then moved relative to the body 56c from the retracted position of FIG. 11 to the extended position of FIG. 10. Once this movement is completed, the trocar can then be removed from the container by moving the body relative to the tube 52c from the retracted position to the extended position.

The principles of the present invention can also be used to provide apparatus for mixing the fluids in container 22. One such mixing device is shown and described in FIGS. 12 and 13. In the apparatus shown, holder 12e and foot member 18e have been modified wherein the foot member is mounted on bearings 160 so that the member rotates relative to the holder 123 about axis 34. The head member 30e is mounted on the end of a drive shaft 162 along axis 34. Means in the form of rack and pinion gears 168 and 170, are provided for moving the platform 166 and motor 164 along axis 34. Gear 168 is mounted on planar member 172 which is slidable in a direction parallel to axis 34 by means of guideways 174. Rotation of gear 170 causes planar member 172 to move in guideways 174, so that platform 166, motor 164 and shaft 162 move along axis 34. By suitably connecting the leads of motor 164 to a power source, rotation is imparted to shaft 162 and head member 30e.

When mixing fluid in container 22, container 22 is placed in the holder in a manner described in FIG. 2. The holder and container are placed under foot member 30e, and the platform 166 which is initially in its raised position is moved by rotating gear 170 which imparts linear motion to gear 168 to move the platform 166 together with the motor 164, shaft 162 and head member 30e into contact with the upper end of container 22. As the head member 30e engages the container, the container will move into alignment with axis 34. Since the foot member 18e is mounted on bearings 160, as pressure is provided by head member 30e on the top end 26 of container 22, the container will begin to rotate about axis 34. When mixing is completed the head member 30e can be moved up and away from the container 22 by rotating gear 170 in the opposite direction so that gear 168 together with platform 166 moves in an upward direction. As head member 30e moves away from the top of container 22 the latter will stop rotating.

Another device useful in mixing fluids in container 22 which utilizes the principles of the present invention is shown in FIG. 14. The apparatus includes the holder 12f together with the head member 30f and foot member 18f. In this apparatus the foot member 18f is connected to a linkage arm 178 which is pivotably attached to the foot member 18f in the aperture 38 of the latter. The linkage arm extends through the aperture 40 of the holder 12f where the opposite end is connected to a rotatable wheel or cam 180, at a point which is off center of the rotation axis of the latter. The arm 178 is of a length so that the head member 30f will move up and down in the holder with a complete rotation of cam 180. Rotation of cam 180 thus imparts a reciprocal vertical movement of the linkage arm 178 such that the foot member 18f together with container 22 will move up and down in the holder 12.

When mixing fluid in container 22, the container is dropped in the holder 12 and positioned in a similar manner as described in reference to FIG. 2. The head member 30f is dropped in holder 12 so as to center the container about the axis 34. The wheel 180 is then rotated so that the foot member 18f together with container 22 and head member 30f move up and down along the axis 34. This up and down motion will result in the mixing of the fluids in container 22. The principles of the present invention can also be applied so as to provide means for ejecting the container 22 from the holder 12. For example, the apparatus described in FIG. 14 can be modified so that cam 180 rotates from a first position in which the foot member 18f is disposed at the bottom of holder 12 to a second position wherein head member 30f is moved upwardly and out the top end 16 of holder 12f. In this second position the top end 26 of container 22 extends out the top end of the holder and thus can be easily removed. The embodiment thus described in FIG. 14 utilizes mechanical means to eject the container 22 from holder 12. It will be appreciated however, that other types of systems can be used to eject the container, such as pneumatic types.

Figure 16:
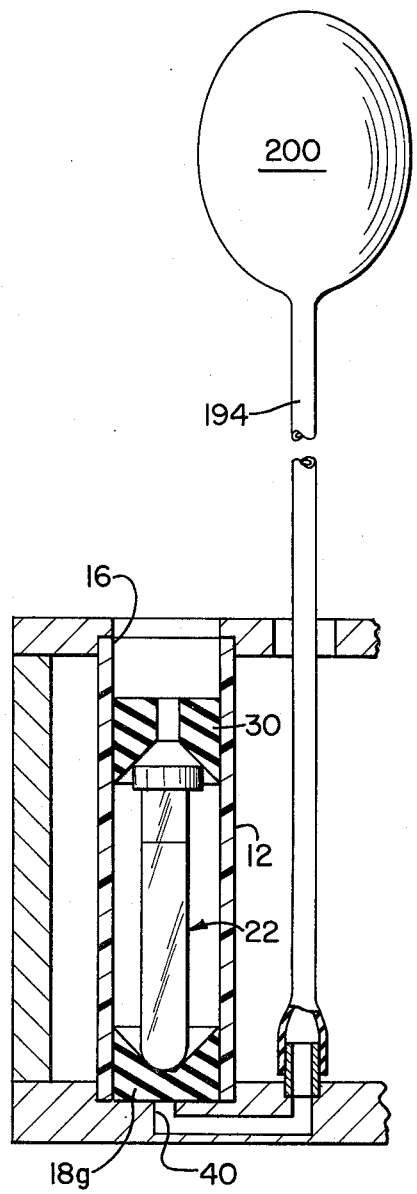
FIG. 16 illustrates in cross-section, a second embodiment of the present invention including means for ejecting the container.

Referring to FIGS. 15 and 16, two such pneumatic types of apparatus are described in detail. In FIG. 15 a source of compressed gas 190 is connected through valve 192 by conduit 194 to aperture 40 of holder 12. In this embodiment foot member 18g has been modified so that there is no opening corresponding to aperture 38 but instead, member 18g completely but slidingly occludes holder 12. By opening and closing valve 192, the compressed gas is introduced through conduit 194 into the holder. Foot member 18g acts as a piston so that the container and head member (not shown) are moved to the top end 16 of the holder where the head member and container can be removed.

In the apparatus shown in FIG. 16 the source of pressurized gas is provided in the form of a commpressible and resilient bulb 200 attached through conduit 194 to aperture 40 of holder 12. By squeezing bulb 200, air passes through conduit 194 and forces unapertured foot member 18g together with the container 22 and head member 30 to the top end 16 of the container 12.

The principles of the present invention thus provide an easy and simple device for centering elongate sample containers, regardless of their size so that they may be easily placed and oriented along a predetermined axis. Once properely oriented, the samples may be mixed or tested with a probe or aspirated or dispensed out of or into the container. The use of the container head and foot members provide an easy method of performing the above functions when the container is partially immersed in a fluid, for example when the containers are immersed in a fluid in order to maintain the samples at a constant temperature. Since all functions can be performed through the top end of the holder, the holder need not be removed from the fluid in which the holder is immersed.

Since certain changes may be made in the above apparatus without departing from the scope of the invention herein involved, it is intended that all matter contained in the above-description or shown in the accompanying drawings shall be interpreted in an illustrative and not in a limiting sense.

What is claimed is:

1. A device for orienting an elongate container along a predetermined axis comprising:
   means defining a first tapered cavity for receiving one end of said container;
   means for supporting the other end of said container in a temporary position when said one end is disposed in said first tapered cavity; and
   means defining a second tapered cavity for receiving said other end of said container;
   said means defining said first tapered cavity and said means defining said second tapered cavity being movable relative to one another so that during relative motion of said means defining said first and second cavities toward one another, said other end of said container is engaged by said second cavity and is moved from said temporary position to bring said container into alignment with said predetermined axis.

2. A device in accordance with claim 1, wherein at least one of said first and second tapered cavities is of a substantially conical shape.

3. A device in accordance with claim 1, wherein at least one of said first and second cavities is of a substantially frusto-conical shape.

4. A device in accordance with claim 1, wherein said means for supporting said other end of said container comprises a hollow cylinder having a minimum cross-sectional dimension which is greater than the maximum cross-sectional dimension of said container and wherein said first and second tapered cavities each has a maximum cross-sectional dimension substantially greater than the maximum cross-section dimension of said container.

5. A device in accordance with claim 4 wherein said means cross-sectional shape tapered cavity is mounted for sliding movement along said axis within said cylinder.

6. A device in accordance with claim 4, wherein the internal cross sectional shpae of said cylinder is circular.

7. A device in accordance with claim 4 further including means for ejecting said container from said hollow cylinder.

8. A device in accordance with claim 7 wherein said means for ejecting includes a rotatable cam and a linkage arm having two opposite ends, one of said ends being connected to said cam and the other of said ends being connected to said means defining said first tapered cavity so that rotation of said cam moves said means defining said first cavity axially in said cylinder.

9. A device in accordance with claim 7 wherein said means for ejecting said container from said hollow cylinder includes means for introducing pressurized fluid into said cylinder so that introduction of said fluid moves said means defining said first cavity axially in said cylinder.

10. A method of centering an elongate container along a predetermined axis comprising the steps of placing one end of the container in a first tapered cavity while resting the other end of the container in a temporary position, and
   moving the first tapered cavity and a second tapered cavity disposed near the other end of the container relative to one another so that the second tapered cavity engages the other end of the container and moves the container into alignment with said predetermined axis.

11. Apparatus for testing aspirating and dispensing sample fluids in elongate containers comprising:
   means defining a first tapered cavity for receiving one end of said container;
   means for holding the other end of said container in a temporary position;
   means defining a second tapered cavity for receiving said other end of said container and moving said container from said temporary position into alignment with a predetermined axis;
   means for moving a trocar along said predetermined axis relative to said means defining said second cavity between a first position wherein the trocar extends into said container and a second position wherein said trocar is disposed outside of said container;
   probe means movable within and relative to said trocar along said predetermined axis between a retracted postion wherein said probe means is retracted into said trocar and an extended position wherein said probe means extends out of said trocar into said container.

12. Apparatus in accordance with claim 11 wherein said means for holding the other end of said container in a temporary position comprises a hollow cylinder having a minimum cross-sectional dimension which is greater than the maximum cross-sectional dimension of said container.

13. Apparatus in accordance with claim 12 wherein said means defining a second tapered cavity includes a tubular member and means formed at one end of said member defining said second tapered cavity, said tubular member being slidable in said hollow cylinder so that as said tubular member slides in said hollow cylinder said second tapered cavity engages said other end of said container and moves said container into alignment with said predetermined axis.

14. Apparatus in accordance with claim 13 wherein said means defining said second tapered cavity includes an aperture at the bottom of said cavity into said tubular member, and wherein said means for moving said trocar includes a tubular body having one end connected to said trocar and being slidable in said tubular member between said first and second positions wherein said trocar is capable of moving in and relative to said aperture when moving between said first and second positions.

15. Apparatus in accordance with claim 14 further including means for biasing said body in said first position.

16. Apparatus in accordance with claim 15 further including means for locking said tubular body relative to said tubular member in any position between and including said first and second positions.

17. Apparatus in accordance with claim 15 wherein said means for biasing includes a compressible helical spring mounted in said tubular member for urging said tubular body and said trocar away from the end of said tubular element provided with said second tapered cavity.

18. Apparatus in accordance with claim 14 wherein said probe means includes a syringe cartridge and a cannula attached to one end of said cartridge, said cartridge being slidable in said tubular body between said extended and retracted positions, wherein said cannula is capable of moving in a coaxial direction with and relative to said trocar between said retracted and extended positions.

19. Apparatus in accordance with claim 18 further including second means for biasing said cartridge in said extended position.

20. Apparatus in accordance with claim 19 further including means for locking said cartridge relative to said tubular body in any position between and including said retracted and extended positions.

21. Apparatus in accordance with claim 19 wherein said second means for biasing includes a compressible helical spring mounted in said tubular body and urging said cartridge and said cannula away from the end of said body provided with said trocar.

22. Apparatus in accordance with claim 18 wherein said cartridge includes a plunger for drawing and dispensing fluids through said cannula.

23. Apparatus in accordance with claim 18 further including means for limiting the movement of said tubular body relative to said tubular member between said first and second position.

24. Apparatus in accordance with claim 23 wherein said means for limiting the movement of said tubular body includes an axially-directed slot formed in said tubular member, and a pin connected to said tubular body and radially extending through said slot.

25. Apparatus in accordance with claim 14 wherein said probe means includes a plunger and sensing means attached to one end of said plunger, said plunger being slidable in said tubular body between said extended and retracted positions, wherein said sensing means is capable of moving in a coaxial direction with and relative to said trocar between said retracted and extended positions.

26. Apparatus in accordance with claim 25 wherein said probe means includes a pH electrode.

27. Apparatus in accordance with claim 14 further including means for introducing cleaning fluid into said tubular member and said tubular body so as to rinse the interior and exterior surfaces of said trocar and at least the exterior surface of said probe means.

28. Apparatus in accordance with claim 27 wherein said tubular body is movable to a third position beyond said second position, and wherein said means for introducing cleaning fluid includes a port formed in said tubular member which is closed between said first and second positions and open in said third position.

29. Apparatus in accordance with claim 26 wherein said probe means is movable to a tertiary position beyond said extended position, and wherein said means for introducing cleaning fluid includes a port formed in said tubular body which is closed between said retracted and extended positions and open in said tertiary position.

30. Apparatus for centering sample fluids in elongate containers along a predetermined axis and mixing said sample fluids comprising:
means defining a first tapered cavity for receiving one end of said container;
means for holding the other end of said container in a temporary position;
means defining a second tapered cavity for receiving said other end of said container and moving said container from said temporary position into alignment with said predetermined axis; and
means for moving said container so as to mix the fluid in said container.

31. Apparatus in accordance with claim 30 wherein said means for supporting includes a hollow cylinder having a minimum normal cross-sectional dimension which is larger than the maximum normal cross-sectional dimension of said container.

32. Apparatus in accordance with claim 31 wherein said means for moving said container includes means for reciprocally moving said container along sid predetermined axis.

33. Apparatus in accordance with claim 32 wherein said means defining said first and second tapered cavities each have a cross-sectional shape substantially the same as the internal cross-sectional shape of said hollow cylinder and sized so as to be slidable in said cylinder, and wherein said means for reciprocally moving said container includes a rotatable cam and a linkage arm having two opposite ends, one of said ends being connected to said cam and the other of said ends being connected to said means defining said first tapered cavity so that rotation of said cam reciprocally moves said container along said predetermined axis.

34. Apparatus in accordance with claim 31, wherein said means defining said first tapered cavity is mounted in said cylinder for rotation about said predetermined axis and wherein said means defining said second tapered cavity is mounted for rotation about said predetermined axis and capable of being moved along said axis, said apparatus further including means for rotating and moving said means defining said second tapered cavity along said predetermined axis.

35. A method of aspirating and dispensing sample fluids out of and into elongate containers, comprising the steps of:
 placing one end of the container in a tapered cavity while resting the other end of the container in a temporary position;
 moving the first tapered cavity and a second tapered cavity disposed near the other end of the container relative to one another so that the second tapered cavity engages the end of the container and moves the container into alignment with a predetermined axis;
 passing a trocar along said predetermined axis through one of said cavities and into said container;
 moving probe means along said predetermined axis through said trocaar into said container;
 aspirating or dispensing fluid out of or into said container;
 moving said probe means along the predetermined axis so as to retract said probe means into said trocar; and
 moving said trocar along said predetermined axis so as to withdraw said trocar from said container and through said one cavity.

* * * * *

UNITED STATES PATENT OFFICE
CERTIFICATE OF CORRECTION

PATENT NO. : 3,991,627
DATED : November 16, 1976
INVENTOR(S) : Cleve Watrous Laird et al It is certified that error appears in the above-identified patent and that said Letters Patent are hereby corrected as shown below:

Column 12, claim 5 should read as follows:

5. A device in accordance with claim 4 wherein said means defining said second tapered cavity is mounted for sliding movement along said axis within said cylinder.

Column 12, line 13, "shpae" should read -- shape--;

Column 14, line 48, "sid" should read --said--;

Column 16, line 4, "trocaar" should read --trocar--.

Signed and Sealed this

Fifteenth Day of February 1977

[SEAL]

Attest:

RUTH C. MASON
Attesting Officer

C. MARSHALL DANN
Commissioner of Patents and Trademarks